(12) United States Patent
Toth et al.

(10) Patent No.: US 6,327,331 B1
(45) Date of Patent: Dec. 4, 2001

(54) METHOD AND APPARATUS FOR ANALYZING CT Z-AXIS BEAM POSITIONING

(75) Inventors: Thomas L. Toth, Brookfield; Steven J. Woloschek, Franklin, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/473,346

(22) Filed: Dec. 28, 1999

(51) Int. Cl.[7] .................................................. G01S 23/00
(52) U.S. Cl. .............................. 378/20; 378/4; 378/207; 378/901
(58) Field of Search ............................... 378/207, 20, 19, 378/4, 901

(56) References Cited

U.S. PATENT DOCUMENTS

| | | | |
|---|---|---|---|
| 4,991,189 | 2/1991 | Boomgaarden et al. ................. | 378/4 |
| 5,610,963 | * 3/1997 | Hsieh ..................................... | 378/151 |
| 5,761,257 | 6/1998 | Toth et al. .............................. | 378/19 |
| 6,056,437 | * 5/2000 | Toth ...................................... | 378/205 |

OTHER PUBLICATIONS

U.S. application No. 09/199,170, Filed Nov. 24, 1998.
U.S. application No. 08/576,066, Filed Dec. 21, 1995.
U.S. application No. 09/384,937, Filed Aug. 27, 1999.
U.S. application No. 09/384,169, Filed Aug. 27, 1999.

* cited by examiner

*Primary Examiner*—Drew Dunn
(74) *Attorney, Agent, or Firm*—Armstrong Teasdale LLP; Christian G. Cabou (57) ABSTRACT

In one embodiment of the present invention, a method is provided for analyzing performance of tracking control loop in a CT imaging system configured to position an x-ray beam using the tracking control loop. The method includes the steps of collecting control loop data over a plurality of views during scanning and of evaluating control loop data relative to the corresponding views to measure at least one imaging system characteristic. This method provides the imaging system user with data that facilitates insight into possible causes for imaging artifacts. In another embodiment, a CT imaging system is provided including a tracking control loop. The CT imaging system is configured to position an x-ray beam using the tracking control loop, collect control loop data over a plurality of views during scanning and evaluate control loop data relative to the corresponding views to measure at least one imaging system characteristic.

22 Claims, 4 Drawing Sheets

METHOD AND APPARATUS FOR ANALYZING CT Z-AXIS BEAM POSITIONING

BACKGROUND OF THE INVENTION

This invention relates generally to computed tomography (CT) imaging and, more particularly, to methods and apparatus for analyzing performance of x-ray beam positioning by a z-axis tracking loop in a multi-slice CT imaging system.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

A closed-loop z-axis control system can be used to position an x-ray beam relative to a detector array. An x-ray beam could be maintained at a position very close to a detector array edge by repositioning a collimator in response to a measured beam position, however, a malfunctioning z-axis control loop can cause image artifacts, particularly in imaging data collected from outer rows of the detector array. However, image artifacts are not solely caused by control loop error, so it would be desirable to provide methods to verify that a control loop is performing as expected. It also would be desirable to provide methods for analyzing effects of other imaging system characteristics, e.g. mechanical dynamic skew, on control loop performance.

BRIEF SUMMARY OF THE INVENTION

There is therefore provided, in one embodiment, a method for analyzing performance of a tracking control loop in a CT imaging system configured to position an x-ray beam using the tracking control loop, the method including steps of collecting control loop data over a plurality of views during scanning and of evaluating control loop data relative to the corresponding views to measure at least one imaging system characteristic.

The above-described method provides the imaging system user with data that facilitates insight into possible causes for imaging artifacts.

DETAILED DESCRIPTION OF THE INVENTION

Figure 1:
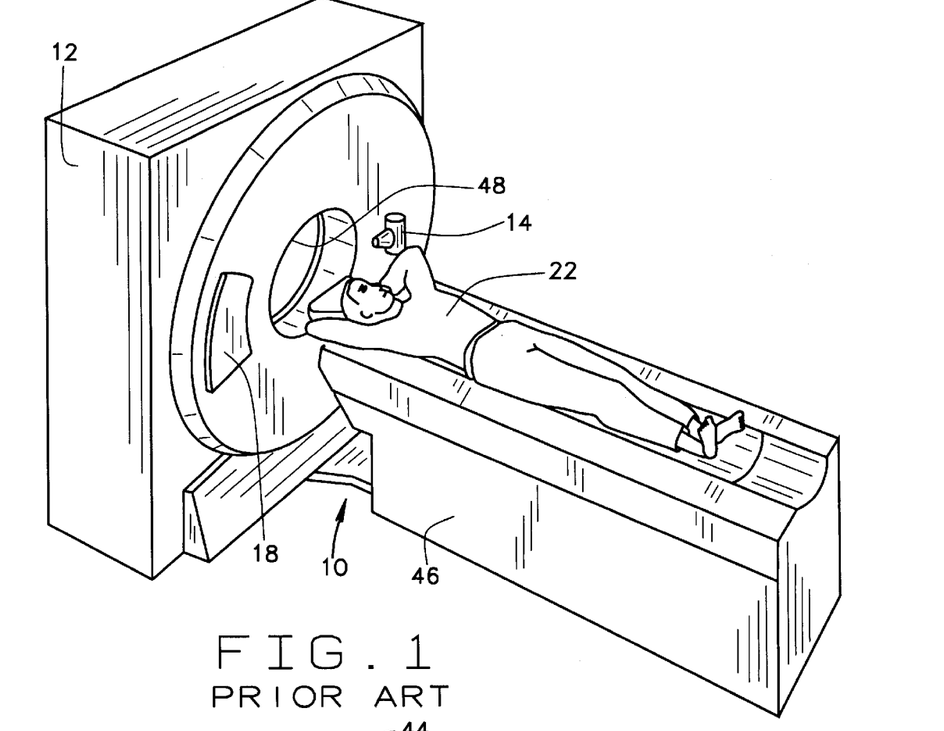
FIG. 1 is a pictorial view of a conventional CT imaging system.
Figure 2:
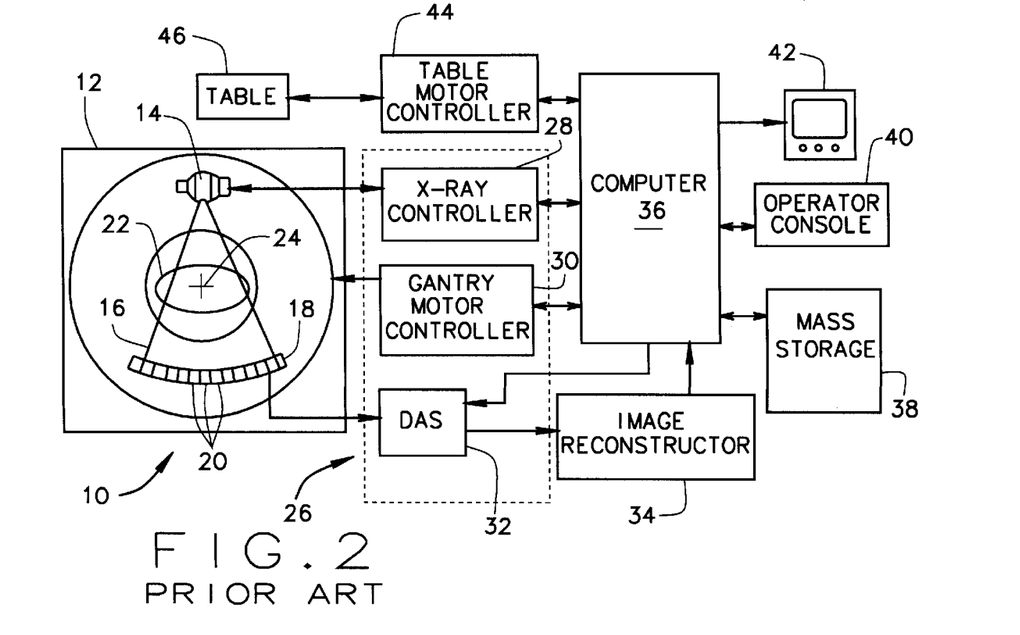
FIG. 2 is a block schematic diagram of the conventional system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14, for example an x-ray tube, that projects a beam of x-rays 16 toward a detector array 18 on the opposite side of gantry 12. Detector array 18 is formed by detector elements 20 that together sense the projected x-rays that pass through an object 22, for example a medical patient. Detector array 18 is fabricated in either a single slice or a multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation or isocenter 24.

Rotation of gantry 12 and the operation of x-ray source 14 are governed by a control mechanism 26 of CT system 10. Control mechanism 26 includes an x-ray controller 28 that provides power and timing signals to x-ray source 14. Control mechanism 26 also includes a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 that stores the image in a mass storage device 38.

Computer 36 also receives commands and scanning parameters from an operator (not shown) via console 40 that has a keyboard. An associated cathode ray tube display 42 allows the operator to observe the reconstructed image and other data from computer 36. The operator-supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 in gantry 12. Particularly, table 46 moves portions of patient 22 through gantry opening 48. Gantry 12 includes a window (not shown) that permits transmission of x-ray beam 16 through a plastic gantry cover (also not shown) while protecting x-ray source 14 from spills of, for example, contrast media or patient fluids that may occur during scanning.

Figure 3:
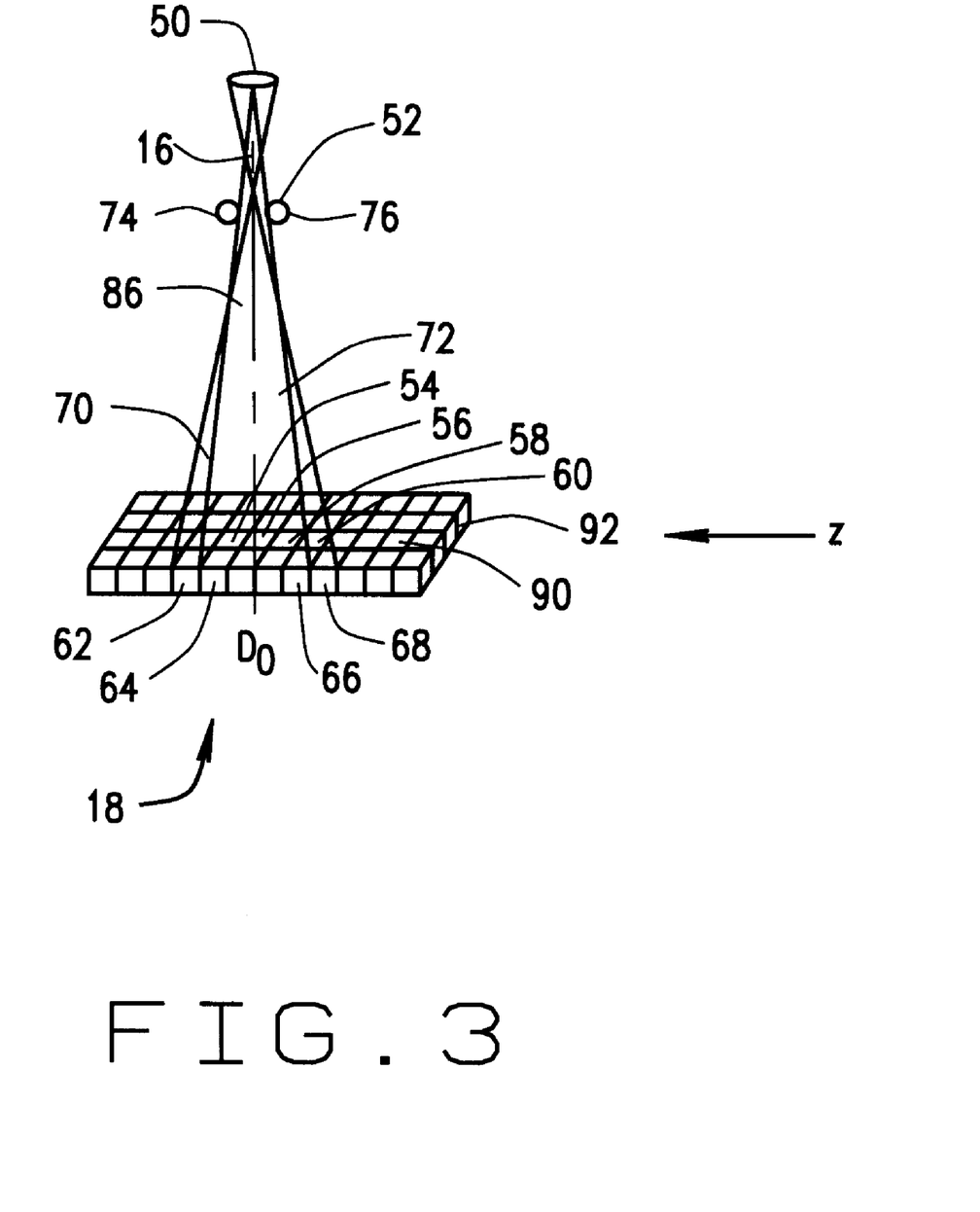
FIG. 3 is a schematic view of a portion of the CT imaging system shown in FIG. 1 showing an embodiment of a z-axis positioning system.

In one embodiment and as shown in FIG. 3, x-ray beam 16 emanates from a focal spot 50 of x-ray source 14 (FIG. 2). X-ray beam 16 is collimated by a collimator 52, and collimated beam 16 is projected toward detector array 18.

Detector array 18 is fabricated in a multi-slice configuration and includes detector element rows 54, 56, 58 and 60 for projection data collection. A plane 86, generally referred to as the "fan beam plane", contains the centerline of focal spot 50 and the centerline of beam 16. Fan beam plane 86 is illustrated in FIG. 3 as being aligned with a centerline $D_0$ of detector array 18, although fan beam plane 86 will not always be so aligned. Detector element rows 62, 64, 66 and 68 of detector array 18 serve as z-position detectors for determining a z-axis position of x-ray beam 16. Outer rows 62 and 68 are selected to be substantially within penumbra 70 of beam 16. Inner rows 64 and 66 are selected to be substantially within umbra 72 of beam 16. Outer row 62 and 68 signal intensities thus depend on an x-ray beam position, and inner row 64 and 66 signal intensities provide references against which outer row signals are compared. Alignment of detector rows 62, 64, 66 and 68 as shown in FIG. 3 is exemplary only, and is different in at least one other embodiment. Collimator 52 includes tapered cams 74 and 76, and thus is sometimes referred to as a "cam collimator." (Where it is stated herein that a cam "has a taper," it is not intended to exclude cams having a taper of zero unless otherwise stated.) X-ray controller 28 controls positioning of cams 74 and 76. Each cam can be independently positioned to alter position and width of x-ray umbra 72 relative to an edge 92 of detector array 18.

Figure 4:
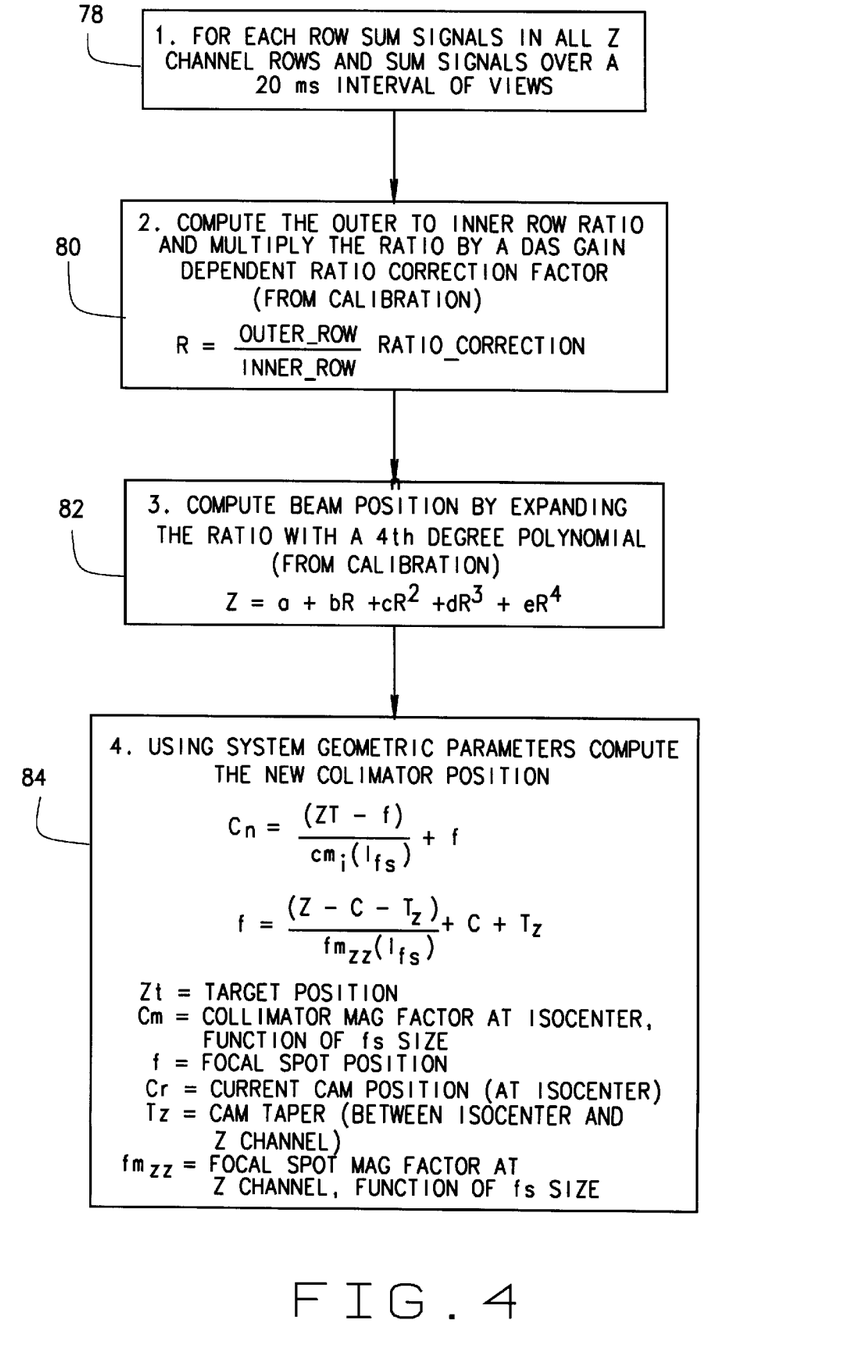
FIG. 4 is a flow diagram an embodiment of a z-axis tracking control loop.

In one embodiment, and as shown in FIG. 4, a closed-loop method for positioning beam 16 comprises comparing signals representative of x-ray intensity received from different rows of detector elements and positioning an x-ray beam in accordance with results of the comparison. Signals representative of x-ray intensity from detector rows 62, 64, 66, and 68 are summed 78 over views in a 20 millisecond interval to obtain row sums. For example, after the analog signals are converted to a digital format, hardware circuitry (not shown) in DAS 32 performs offset correction and determines row sums from signals received from outer row 62 and from inner row 64. A corrected ratio R is determined 80 by determining a ratio of a sum of signals received from outer row 62 to a sum of signals received from inner row 64 and multiplying the ratio by a ratio correction factor. The ratio correction factor, determined from imaging system 10 calibration, accounts for different relative DAS gains between outer row 62 and inner row 64.

Beam position Z(R) is the determined 82, in millimeters relative to a centerline. Beam position Z is obtained by applying a predetermined beam position transfer function to the corrected ratio to calculate the x-ray beam position. The beam position transfer function Z(R) is represented, for example, by a fourth-degree polynomial having predetermined coefficients:

$$Z(R) = a + bR + cR^2 + dR^3 + eR^4.$$

Beam position transfer function Z(R) and its limits are specified at imaging system 10 calibration.

A new collimator position is then determined 84. A focal spot position f is determined 84 from beam position Z, current collimator position C, and other system 10 geometric parameters in accordance with:

$$f = \frac{(Z - C - T_z)}{fm_{zz}(l_{fs})} + C + T_z,$$

where $T_z$ represents a current taper of cam 74, $fm_{zz}$ represents a focal spot magnification factor at rows 62 and 64 and is a function of focal spot size, and $l_{fs}$ represents focal spot 50 length. A new position for collimator 52 then is determined 84 for a detector element 20 positioned toward isocenter 24. Collimator 52 is repositioned where an edge (not shown) of collimator 52 would meet a line between focal spot position f and a target beam position $Z_t$ that has been specified at imaging system 10 calibration. New collimator position $C_n$ thus is determined in accordance with an equation written as:

$$C_n = \frac{(Z - f)}{cm_i(l_{fs})} + f$$

where $cm_i$ represents a current collimator magnification factor at detector element 20 positioned toward isocenter 24 and is a function of focal spot size, and $l_{fs}$ represents focal spot 50 length.

In one tracking loop embodiment, steps 78, 80, 82, and 84 are performed independently for each side of collimator 52 at intervals to continuously obtain new positions for each side of collimator 52. These intervals are, in one embodiment, 20 milliseconds, to sample the x-ray beam 16 position 25 times during a 0.5 second scan to minimize control loop lag error. However, in other embodiments, the interval is between 5 milliseconds and 50 milliseconds. In still other embodiments, the interval is between a minimum value sufficient to avoid effects of quantum noise and high frequency variation (such as due to x-ray tube anode movement at a run frequency between 50 Hz and 160 Hz) and a maximum constrained by a slew rate of the sag curve. Sampling the changing sag curve frequently avoids excessive positioning error. (Sag is a periodic movement of x-ray beam 16 resulting from gravity and from centrifugal forces acting on mechanical structure during a rotation of gantry 12.)

During patient scanning, z-position detectors 62, 64, 66 or 68 may become blocked by patient clothing, blankets, or other object. After blockage of a z-position detector 62, 64, 66, or 68 has been detected, or when x-ray source 14 first turns on, the loop sample interval is adjusted downward. In one embodiment, the loop sample interval is adjusted downward to 5 milliseconds. After 4 milliseconds of stabilization, the position of the beam is measured and collimator positioning is started to further minimize initial position errors.

During a blockage, loop operation is suspended. To determine if any z-position detectors are blocked, a signal from a last data detector element 90 adjacent a z-position detector 62, 64, 66 or 68 is compared to an expected signal Sx. Z-position detector blockage is assumed, in one embodiment, if a last data detector element 20 signal is less than 0.9 times expected signal Sx. In other embodiments, detector blockage is assumed when a last data detector element 20 signal is less than a value between 0.95 and 0.5 times expected signal Sx. (It is desirable to make this value as large in magnitude as possible to identify patient blockage as quickly as possible, thereby avoiding mispositioning of x-ray beam 16 due to corrupted Z-measurement data. A maximum of 0.95 is used in one embodiment because it is known that x-ray scatter blockage from large patients 22, for example, can reduce a signal to 0.95 times the expected value.) During a blockage, collimator positioning is suspended. However, position measurement continues at an interval that is decreased from 20 to 5 milliseconds. The decreased measurement interval allows imaging system 10 to more quickly detect an end of the blockage and to resume closed-loop positioning.

Expected signal Sx is written as:

$$S_x = gmA * csf * t * g,$$

where gmA is a generator current mA signal proportional to an x-ray source 14 energizing current, csf is a scale factor determined at system 10 calibration, t is a DAS sample time period, and g is a gain factor. Gain factor g allows expected signal $S_x$ to be adjusted according to a gain value used for scanning. In one embodiment, this gain value is selectable from a plurality of gain values available in system 10.

In one embodiment, closed loop tracking is suspended when signal corruption is detected. Signal corruption is detected, for example, by determining an actual focal spot length from a beam position and a collimator position, and comparing the actual focal spot length to a nominal focal spot length. When a difference of, for example, more than 0.1 millimeter is detected between the actual focal spot length and the nominal spot length, corruption is assumed to exist and collimator positioning is suspended. (In other embodiments, a difference threshold for assuming corruption is as small as 0.05 millimeter or as large as about 0.6 millimeter. In still other embodiments, a value is selected between a lower limit set by higher probabilities of false activation due to noise, x-ray scatter and/or momentary beam position disturbances and an upper limit that still provides some of the advantages of tracking.) However, beam position measurement continues at a decreased interval, as when a blockage is detected. Such corruption may occur, for example, for a short time just prior to or just following detection of a patient blockage. If the corruption persists, for example, over 90° of rotation of gantry 12 without detecting a patient blockage, a malfunction of the tracking system requiring servicing has likely occurred. In such an event, a scan is immediately aborted to avoid patient dose and collection of non-diagnostic quality images. In other embodiments, a limit is set from as little as 45° to as much as 360° of a rotation of gantry 12. In other embodiments, a limit is set between a value at which a false alarm rate due to scatter and/or an occasional exceptionally long partial patient 22 blockage is acceptable and an upper limit representing a design choice as to how long compromised operation (high dose and/or non-diagnostic quality images) can be tolerated before terminating a scan.

After system 10 has been switched off, position of focal spot 50 changes as source 14 cools over time. In one embodiment, before system 10 is switched on again, an initial focal spot position is approximated from information obtained when a focal spot position was last measured. An approximation of a linear function is used to model focal spot position change during cooling in one embodiment, and in another embodiment, the linear function is a 97 nanometer per second linear function. Because position change with cooling is an exponential function, the linear approximation is clamped at 0.15 millimeters. This clamping corresponds to approximately 20% of a cooling change in system 10 when fully cold, where a linear approximation to the exponential function suffices. A fully cold position requires 8 to 12 hours without patient scanning, and a tube warm up prior to patient scanning is normally requested if the tube has been off more than 1 hour. Therefore, a fully cold position, although possible, is not likely during normal patient scanning. During tube warm up a current measured position of the focal spot is established again for initial positioning of the collimator.

Figure 5:
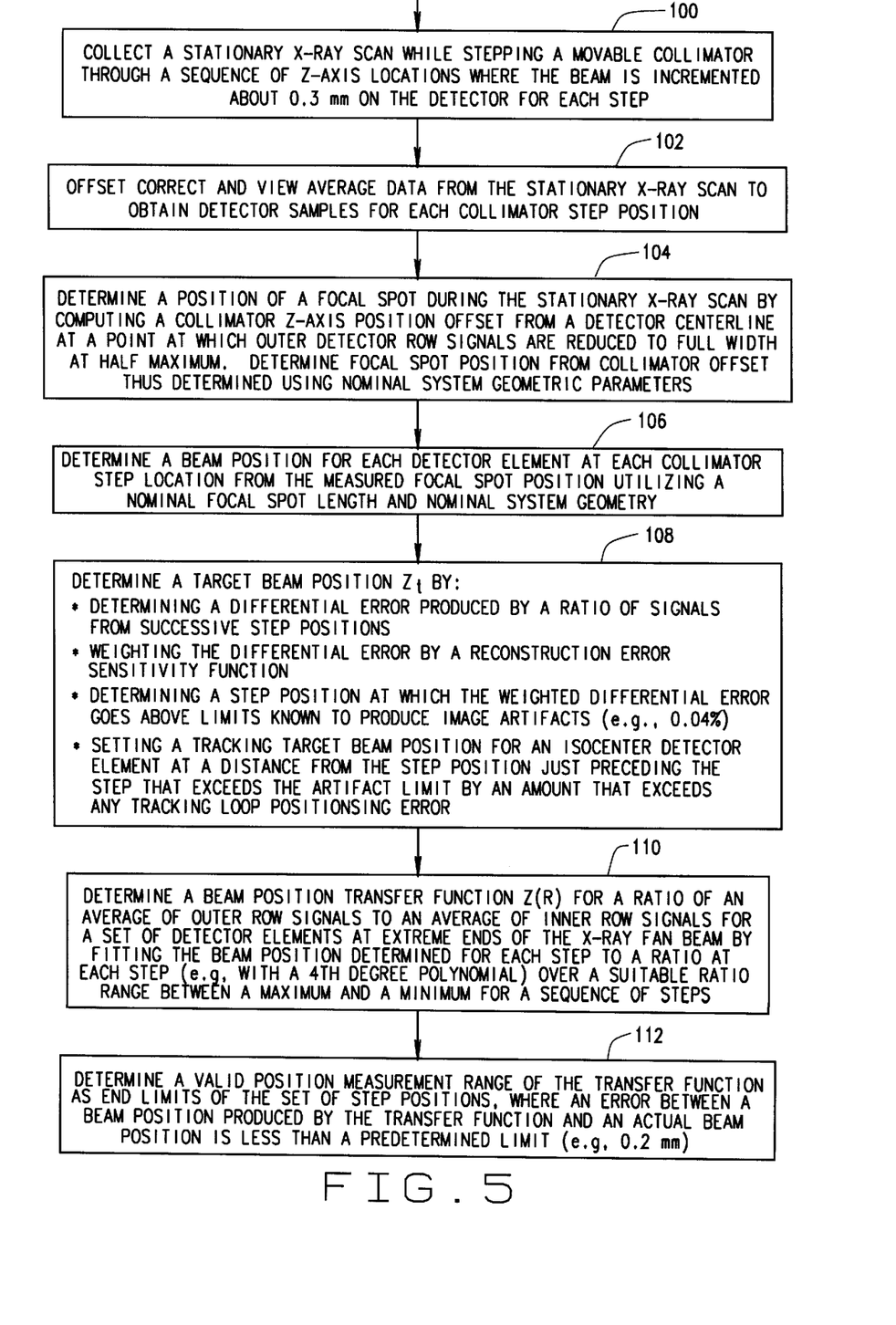
FIG. 5 is a flow diagram of a method for calibrating tracking control loop parameters.

Several tracking loop parameters described herein, specifically, beam position transfer function Z(R) and its limits and target beam position $Z_t$, are determined at system 10 calibration. FIG. 5 illustrates one embodiment of a method for calibrating tracking loop parameters. In this embodiment, data from a stationary sweep scan is collected 100 while collimator 52 is stepped through a sequence of z-axis positions. Beam 16 is incremented 0.3 millimeters on detector array 18 exposure surface for each collimator 52 step position. The sweep scan data is offset-corrected and view averaged 102 to obtain a set of detector samples for each collimator 52 step position. A position of the focal spot is then determined 104. A collimator 52 z-axis position offset from detector array centerline $D_0$ is determined 104, as the point where outer rows 62 and 68 receive signals of half-maximum intensity at full detector element 20 width. Position of focal spot 50 during sweep scan then is determined 104 from collimator 52 z-axis offset and nominal system 10 geometric parameters.

A beam 16 position is determined 106 for each detector element 20 at each collimator 52 step position. Beam 16 positions are determined from sweep scan focal spot 50 position, nominal length of focal spot 50, and nominal system 10 geometry.

Target beam position Z, then is determined 108 for detector element 20 positioned toward isocenter 24. When beam 16 is directed at target beam position $Z_t$, beam 16 is sufficiently close to detector array 18 edge 92 to prevent imaging artifacts but is far enough away to minimize patient dosage. To determine target beam position $Z_t$, ratios of detector samples for successive collimator 52 step positions are utilized to determine a detector differential error. A reconstruction error sensitivity function w(i) then is applied to weight the detector differential error. Reconstruction error sensitivity function w(i) is related to the percent positive contribution of a detector element 20 as a function of its radial distance from isocenter 24. Function w(i), in one embodiment, is computed from nominal system geometry. In another embodiment, w(i) is empirically determined. For example, the following equations describe an empirical determination of w(i):

$$b(i) = 0.018, \ 0 \leq i \leq 5$$

$$b(i) = 0.035 + 0.00075 \times (i-5), \ 5 \leq i \leq 213$$

$$b(i) = 0.414 + 0.00365 \times (i-213), \ 214 \leq i \leq n$$

where i represents detector element position from isocenter 24 and b(i) represents an artifact threshold, i.e. a percent differential error, for a double detector element 20 error. Reconstruction error sensitivity function w(i) then is determined in accordance with:

$$w(i) = 0.18/b(i).$$

A collimator 52 step position SP is determined for which the weighted detector differential error exceeds a limit L empirically known to produce image artifacts, for example, 0.04 percent. Target beam position $Z_t$ then is set for the isocenter detector element at a distance just preceding SP by an amount exceeding applicable tracking loop positioning error.

Beam position transfer function Z(R) then is determined 110 for a ratio R of an average of outer row 62 to inner row 64 signals for a set of detector elements at an extreme end of x-ray fan beam 16. Beam 16 positions, determined 106 for each collimator 52 step position, are fitted to the ratio for each collimator 52 step position with a fourth-degree polynomial, for example, in accordance with:

$$Z(R) = a + bR + cR^2 + dR^3 + eR^4$$

over a suitable ratio range between a maximum and minimum for the sequence of steps.

A valid position measurement range for Z(R) is determined 112 as between end limits of the set of collimator 52 step positions for which an error between a beam 16 position determined by Z and an actual beam 16 position is less than a predetermined limit, for example, 0.2 millimeters. In other embodiments, the predetermined limit is between 0.1 millimeters to 0.6 millimeters. In still other embodiments, the predetermined limit is set at a value between a lower limit just above a value at which a range of beam 16 position that can be precisely measured is too limited, and just below a lower limit that is deemed to create tracking errors so large as to unacceptably compromise the benefits of tracking.

As described above, in at least one embodiment, a cam collimator 74, 76 is continuously repositioned in response to a measured beam position. However, if the control loop malfunctions, in such an embodiment, image artifacts may result, especially in outer detector rows 62, 68. Because artifacts can have causes other than those resulting from control loop malfunctions, an analysis method is provided to verify proper loop performance as measured, for example, by control loop error, reference polynomial error, and mechanical dynamic skew error.

Control loop error is an indicator of a tracking control loop's ability to position x-ray beam 16 to a target beam position based on a measured beam position. Control loop error performance is evaluated by collecting control loop data over a plurality of views during scanning, and evaluating control loop data relative to the corresponding views to measure at least one imaging system characteristic. For example, a beam position is determined using the control loop, and the beam position is compared to a target beam position to determine a measure of control loop error. In one embodiment, a beam position computed for a detector element 20 positioned to detect at isocenter 24 (i.e. an isocenter detector element 20) is compared with a desired target beam position $Z_t$. A difference in beam position is computed for each side A and B in one embodiment by determining a value R written as:

$$R = \frac{Outer\_row}{Inner\_row} ratio\_correction,$$

which is a corrected ratio correction of the outer and inner row, the ratio correction having been obtained from DAS 32 gain calibration. (Sides A and B refer to halves of detector 18. Detector 18 may be considered as being divided in half by a plane perpendicular to the z-axis. Side A is that half of detector 18 lying on the same side of the plane as the mounting structure for patient table 46 in FIG. 1. Side B is the other half of the detector. The labels given to the halves are arbitrary.) Next, R is transformed to a beam position in mm. In one embodiment, this transformation is written as a fourth-degree polynomial having coefficients obtained from a collimator calibration:

$$Z = a + bR + cR^2 + dR^3 + dR^4.$$

Next, a focal spot position is determined from an equation written as:

$$f = \frac{(Z - C = -T_z)}{fm_{zz}} + C + T_z,$$

where C is a current cam position (at isocenter), $T_t$ is a cam taper at a Z module, i.e., a set of detector channels 62, 64, 66, 68 that are operated in a mode to measure beam position; and $fm_{ZZ}$ is a focal spot magnification factor at the Z module, which is a function of focal spot length $l_{fs}$.

A beam position in Z at an isocenter is then written as:

$$Z_i = (C-f)Cm(l_{fs}) + f,$$

where $Z_i$ is the beam position in Z at isocenter; and $C_m$ is a collimator cam magnification factor at isocenter, which is a function of focal spot length.

An error E is then determined. Error E is written as:

$$E = Z_i - Z_t,$$

where $Z_t$ is a target beam position in mmd (e.g., an operating point for an isocenter channel, i.e., a channel derived from a detector element 20 that intercepts a ray from a center of the focal spot in x-ray tube 14 that passes through the center of gantry rotation 24.) A mean loop error per scan is a mean of the absolute value of the loop error E over all views. In one embodiment, comparing the beam 16 position to a target beam position comprises the step of determining a mean loop error per scan as a mean of an absolute value of control loop error over a plurality of views.

During normal patient scanning, control loop firmware continuously monitors loop error information. In one exemplary embodiment, if loop error is greater than a specified or predetermined limit, for example, 0.3 mmd (i.e., millimeters at detector 18) for a number of counted sample intervals (for example, three), an error message is logged to a service log file. On each beam position, an error count is accumulated if this limit is exceeded, and decremented to a minimum of zero if a sample position is within limits. However, if the loop error is greater than a larger specified or predetermined limit, for example, 0.6 mmd, for a number of counted sample intervals (for example, three), it is assumed that imaging system 10 is not under proper control and the current scan is immediately aborted.

In one embodiment, plotting software is provided to retrospectively plot a choice of control loop data for each scan data set in a scan database. Data is plotted as a function of views either in a default filtered (e.g., 20 point boxcar) format or an unfiltered format, at the option of a user. When individual scan data is plotted as a function of views, scaler information (plotted as a function of scans) is also displayed. Pass/fail criteria is also indicated if criteria are available. In addition to loop error for each side A and B, in an exemplary embodiment, the following parameters can be selectively plotted:

Loop Error Relative to Fast Calibration Beam Position. This parameter is the same as the loop error E above, except that this error is determined relative to a mean beam position during fast calibration (which is stored in a calibration data base) instead of relative to a desired z-target position. This parameter is made available because it is useful to know when a current beam position is no longer the same as when a system was fast calibrated. A difference in operating position as compared to calibrated position can account for image artifacts.

Time to Initialize. This parameter is determined as the time required for an absolute value of filtered loop error to be less than a predetermined or specified amount, for example, 0.1 mmd.

Z Ratio. This parameter is determined as the value R above in the set of equations for determining loop error.

Blocked Z Module. This parameter is determined from views in which a blocked channel condition occurs. A view is considered "blocked" if a filtered signal from one or more inner row channels adjacent to the Z-position detector elements 90 is less than a predetermined value. For example, in one embodiment, a view is considered "blocked" if the filtered signal from either of two detector elements 56 and 58 is less than 0.9×mA×T×G×BC_scale. In this expression, mA is a measured mA DAS 32 count value from an auxiliary channel input, T is a DAS sample period, G is a DAS gain factor for an adjacent detector-DAS channel, and BC_scale is a gain blocked scale factor determined during fast calibration. In addition, a "Percent blocked value per scan" parameter is available, as 100 times a number of blocked views divided by total views.

Cam Positions. During a scan DAS 32 writes position data into a scan data file header for each view. Cam 74, 76 position data is obtained from a scan file header.

Focal Spot Position. This parameter is obtained by determining a focal spot position f, as is done during calculation of loop error.

Focal Spot Size. This parameter is determined as a focal spot position B minus a focal spot position A. In one embodiment, focal spot size is within 0.1 mmf (millimeters at the focal spot) of nominal, during normal loop behavior without blockages.

Cam Ringing. Cam ringing is a vibration of source collimator cams 74, 76. This vibration damps out, and usually is not significant, but it is advantageous to measure and plot to verify that it is not significant. Cam ringing is determined as ($f_s$ size)—filtered ($f_s$ size).

Rotor Run. Rotor run results from high frequency variations that are in phase, such as a small periodic movement of an anode of x-ray tube 14 at the rotor run frequency. Rotor run is determined as ($f_s$ position)—filtered ($f_s$ position).

Another type of error that can occur is reference polynomial error. This type of error occurs when a focal distribution function changes shape due to factors such as aging of x-ray tube 14. To compensate for reference polynomial error, in one embodiment, reference polynomial $Z=a+bR+cR^2+dR^3+dR^4$ is recalibrated periodically. Every time a daily system fast calibration is executed, one tracking station is recalibrated so that each polynomial (one for each side) is updated about every two weeks (e.g., coefficients are recomputed). [A tracking station is the set of parameters for controlling the cams associated with each imaging slice configuration. For example, images are collected with slices of 4×1.25 mm, 4×2.5 mm, 4×3.75 mm, or 4×5 mm with either a large or a small focal spot (8 tracking stations).] In addition, imaging system 10 also compares three beam positions from a high, medium, and low value ratio R. If more than 0.3 mmd of beam position change is measured, a recalibration of all calibration stations is requested. If frequent recalibrations of all stations are requested, an x-ray tube 14 is presumed to be exhibiting an unstable focal distribution function and is tagged for replacement. Instability may also be caused by a faulty DAS 32 or Z-channel detector 62, 64, 66, 68 module.

Imaging system 10 tracks beam 16 based on measurements at one end of detector 18 and uses an algorithm to maintain an isocenter position of beam 16 at a desired target position. Because tracking positions beam 16 to an expected position, it is desirable to provide a direct measurement method to measure isocenter beam position during tracking. This measurement is obtained by operating an isocenter channel in a penumbra of beam 16 (i.e., a measure mode position, or in which penumbra impinges on all of the outer row channels) for testing rather than a normal z-target for patient scanning. Thus, entire detector array 18 is used as a position measurement device, as is done for a Z channel 62, 64, 66, 68. Imaging system 10 can then measure whether the isocenter beam position is actually being held in a proper position as indicated by the Z channel. If large variations are observed, then collimator 74, 76 servicing is indicated. Measure mode uses data obtained during a standard calibration sweep scan to associate outer to inner row ratio with beam position, and provides a method for testing whether beam movement is sufficiently similar over the entire detector channel arc. Slight differences in movement versus fan angle gantry are caused by mechanical flexing of gantry 12 during rotation. Measure mode provides assurance that these beam movements are small enough not to cause artifacts when tracking using the Z-module.

Because artifacts have many causes, it is desirable to allow imaging system 10 to scan and produce an image without tracking, using a wide aperture that does not allow a penumbra of x-ray beam 16 to impinge on an edge of detector 18. To produce such an image, a fast calibration without tracking is performed and then an image is reconstructed. If an artifact is present even though tracking is off, this fact can be used by a service engineer to focus his or her servicing on other potential artifact sources.

During clinical operation, contrast media or patient fluids can spill onto a window (for example, a mylar window) of gantry 12 of imaging system 10 through which x-ray beams 16 emanate. These spills can accumulate to increase attenuation and cause the tracking system to indicate a blocked channel, or the spills can otherwise interfere with normal tracking operation. In one embodiment, during daily fast calibrations, the attenuation of the window is measured by powering x-ray tube to about 80 kV at 20–30 mA and performing a complete scan. The detector signal is measured and variations are observed as a function of rotation angle. Attenuation should be constant as a function of rotation angle, so an attenuation value is obtained for each view. A warning message is reported, for example, on CRT display 42 if attenuation increases by more than a predetermined or specified amount, for example 2.5% or 5%, from a mean value at any angle during a rotation. The warning message reports to the user to check the window for contamination.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other imaging systems, including "fourth generation" CT systems wherein the detector is a full-ring stationary detector and only the x-ray source rotates with the gantry, may be used. Moreover, the system described herein performs an axial scan; however, the invention may be used with a helical scan although more than 360 degrees of data are required. While the invention has been described in terms of various specific embodiments, those skilled in the art will recognize that the invention can be practiced with modification within the spirit and scope of the claims.

What is claimed is:

1. A method for analyzing performance of tracking control loop in a CT imaging system configured to position an x-ray beam using the tracking control loop, said method comprising:
   collecting control loop data over a plurality of views during scanning; and
   evaluating control loop data relative to the corresponding views to measure at least one imaging system characteristic.

2. A method in accordance with claim 1 wherein the imaging system is configured to position an x-ray beam to a target location along a z-axis using the tracking control loop, and the step of collecting control loop data over a plurality of views during scanning comprises the steps of:
   determining a beam position using the control loop; and
   comparing the beam position to the target beam position to determine a measure of control loop error.

3. A method in accordance with claim 2 wherein comparing the beam position to the target beam position to determine a measure of control loop error comprises the step of determining a difference between a computed position of the beam and the target position.

4. A method in accordance with claim 3 and further comprising the steps of accumulating a count of control loop errors greater than a specified or predetermined limit, and providing an error indication when an accumulated control loop error count limit is reached.

5. A method in accordance with claim 4 wherein accumulating a count of control loop errors greater than a specified or predetermined limit comprises, for each beam position sample, a step of incrementing the count when the limit is exceeded and decrementing the count to no less than zero when the sample is not exceeded.

6. A method in accordance with claim 4 further comprising the step of terminating a scan when a limit of a number of sample times a control loop error is greater than a specified or predetermined amount is reached.

7. A method in accordance with claim 3 wherein comparing the beam position to the target beam position to determine a measure of control loop error comprises the step of determining a mean loop error per scan as a mean of an absolute value of control loop error over a plurality of views.

8. A method in accordance with claim 1 wherein the at least one imaging system characteristic is a characteristic selected from the group consisting of control loop error, loop error relative to fast calibration beam position, time to initialize, Z-ratio, blocked Z-module, cam position, focal spot position, focal spot size, cam ringing, and rotor run.

9. A method in accordance with claim 1 wherein the CT imaging system comprises a detector having a plurality of rows, and the CT imaging system is configured to determine a beam position as a polynomial function of a ratio of detector signals from a pair of rows of the detector, and further comprising the steps of periodically recalibrating coefficients of the polynomial, determining errors in a plurality of beam positions after recalibration, and indicate a recalibration requirement when more than a predetermined or specified amount of beam position change is measured.

10. A method in accordance with claim 1 wherein the CT imaging system comprises a data acquisition system including an isocenter channel, and further comprising the steps of operating the isocenter channel in a penumbra of the x-ray beam, measuring an isocenter beam position and providing a collimator servicing indication in response to variations in isocenter beam position.

11. A method in accordance with claim 1 wherein the imaging system includes a gantry window, said method further comprising the steps of:
   comparing window attenuation variation during scanning to a mean window attenuation value obtained during the scan; and
   displaying a message when the window attenuation during scanning exceeds the mean window attenuation value by a maximum expected window attenuation variation.

12. A CT imaging system having a tracking control loop, the CT imaging system being configured to:
   position an x-ray beam using the tracking control loop;
   collect control loop data over a plurality of views during scanning; and
   evaluate control loop data relative to the corresponding views to measure at least one imaging system characteristic.

13. A CT imaging system in accordance with claim 12 further configured to position an x-ray beam to a target location along a z-axis using the tracking control loop, and said CT imaging system being configured to collect control loop data over a plurality of views during scanning comprises said CT imaging system being configured to:
   determine a beam position using the control loop; and
   compare the beam position to the target beam position to determine a measure of control loop error.

14. A CT imaging system in accordance with claim 13 wherein said CT imaging system being configured to compare the beam position to the target beam position to determine a measure of control loop error comprises said CT imaging system being configured to determine a difference between a computed position of the beam and the target position.

15. A CT imaging system in accordance with claim 14 further configured to accumulate a count of control loop errors greater than a specified or predetermined limit, and to provide an error indication when an accumulated control loop error count limit is reached.

16. A CT imaging system in accordance with claim 15 wherein said CT imaging system being configured to accumulate a count of control loop errors greater than a specified or predetermined limit comprises said CT imaging system being configured to increment the count when the limit is exceeded and to decrement the count to no less than zero when the sample is not exceeded, for each beam position sample.

17. A CT imaging system in accordance with claim 15 further configured to terminate a scan when a limit of a number of sample times that a control loop error is greater than a specified or predetermined amount is reached.

18. A CT imaging system in accordance with claim 14 wherein said CT imaging system being configured to compare the beam position to the target beam position to determine a measure of control loop error comprises said CT imaging system being configured to determine a mean loop error per scan as a mean of an absolute value of control loop error over a plurality of views.

19. A CT imaging system in accordance with claim 12 wherein the at least one imaging system characteristic is a characteristic selected from the group consisting of control loop error, loop error relative to fast calibration beam position, time to initialize, Z-ratio, blocked Z-module, cam position, focal spot position, focal spot size, cam ringing, and rotor run.

20. A CT imaging system in accordance with claim 12 further comprising a detector having a plurality of rows, said CT imaging system further being configured to determine a beam position as a polynomial function of a ratio of detector signals from a pair of rows of the detector, to periodically recalibrate coefficients of the polynomial, determine errors in a plurality of beam positions after recalibration, and to indicate a recalibration requirement when more than a predetermined or specified amount of beam position change is measured.

21. A CT imaging system in accordance with claim 12 further comprising a data acquisition system including an isocenter channel, and further configured to operate the isocenter channel in a penumbra of the x-ray beam, to measure an isocenter beam position and to provide a collimator servicing indication in response to variations in isocenter beam position.

22. A CT imaging system in accordance with claim 12 further comprising a gantry window, said CT imaging system further being configured to:

compare window attenuation variation during scanning to a mean window attenuation value obtained during the scan; and display a message when the window attenuation during scanning exceeds the mean window attenuation value by a maximum expected window attenuation variation.

* * * * *